United States Patent [19]
de la Torre et al.

[11] Patent Number: 5,997,515
[45] Date of Patent: *Dec. 7, 1999

[54] SCREW-TYPE SKIN SEAL WITH INFLATABLE MEMBRANE

[75] Inventors: Roger A. de la Torre, Lake St. Louis, Mo.; George D. Hermann; Christopher Eric Thayer, both of Portola Valley, Calif.

[73] Assignee: General Surgical Innovations, Inc., Cupertino, Calif.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/840,104

[22] Filed: Apr. 11, 1997

Related U.S. Application Data

[63] Continuation-in-part of application No. 08/444,396, May 19, 1995, Pat. No. 5,634,911.

[51] Int. Cl.⁶ ..................................................... A61M 5/00
[52] U.S. Cl. .......................... 604/256; 604/246; 604/278; 606/213
[58] Field of Search .................................. 604/174, 175, 604/246, 247, 250, 256, 278, 337; 606/213, 215

[56] References Cited

U.S. PATENT DOCUMENTS

| | | | |
|---|---|---|---|
| 4,738,666 | 4/1988 | Fuqua | 604/280 |
| 5,071,411 | 12/1991 | Hillstead | 604/246 |
| 5,360,417 | 11/1994 | Gravener et al. | 604/278 |
| 5,366,478 | 11/1994 | Brinkerhoff et al. | 606/213 |
| 5,403,336 | 4/1995 | Kieturakis et al. | 606/167 |
| 5,545,179 | 8/1996 | Williamson, IV | 606/213 |
| 5,607,443 | 3/1997 | Kieturakis et al. | 606/192 |

*Primary Examiner*—Corrine McDermott
*Attorney, Agent, or Firm*—Lyon & Lyon LLP

[57] ABSTRACT

A skin seal or trocar stabilizer with an inflatable membrane disposed inside, whereby medical instruments may be passed through the skin seal into a endoscopic work space while the inflatable membrane is inflated, thereby allowing the use of normal short conventional open surgery instruments during endoscopic procedures and during insufflation.

44 Claims, 11 Drawing Sheets

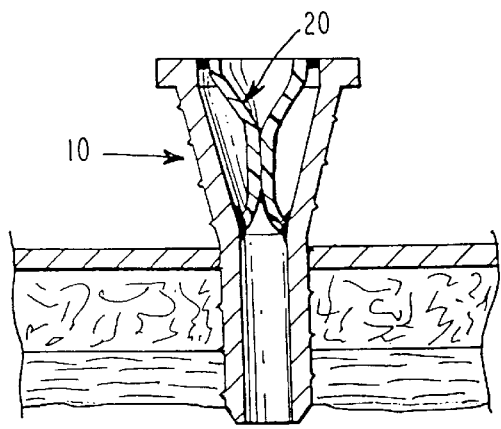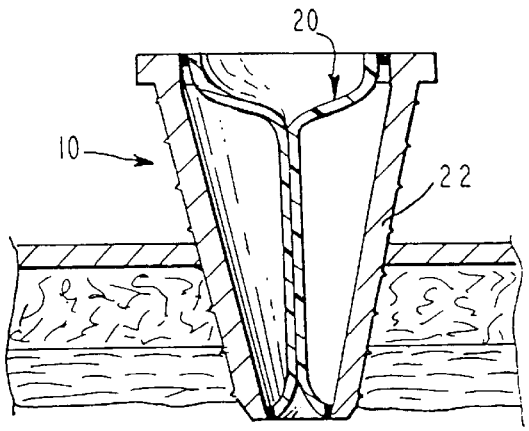
FIG. 6a  FIG. 6b
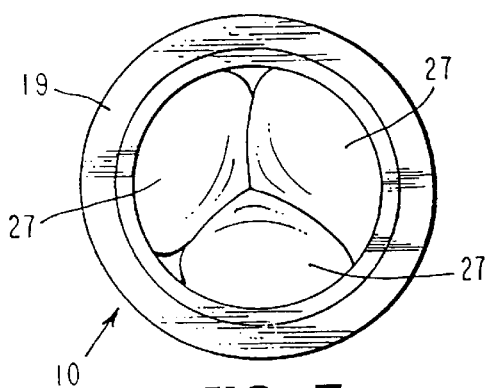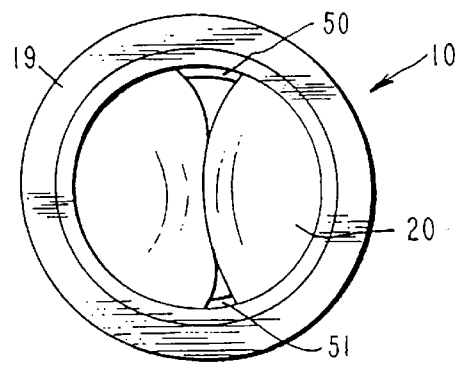
FIG. 7  FIG. 7a
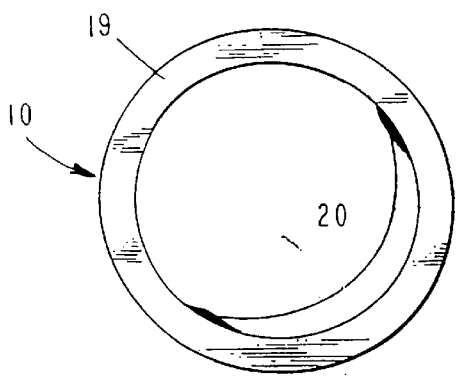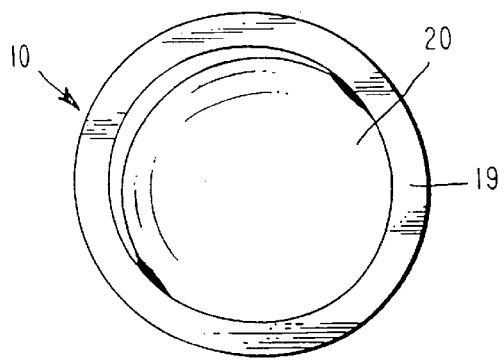
FIG. 7b  FIG. 7c

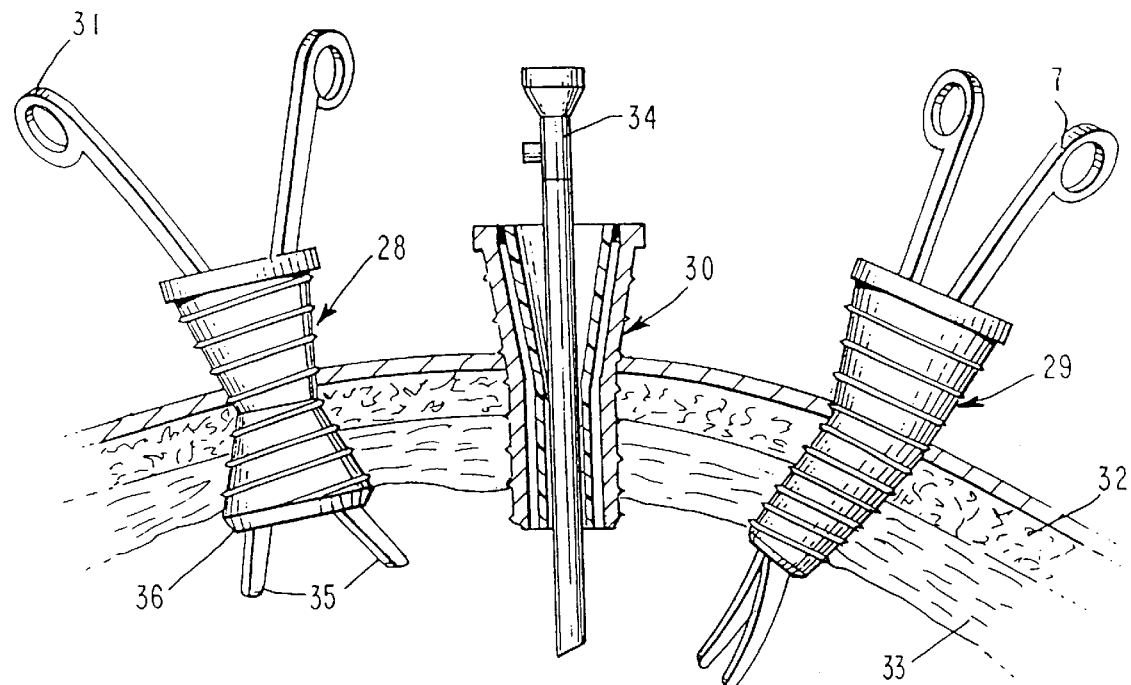
FIG. 8
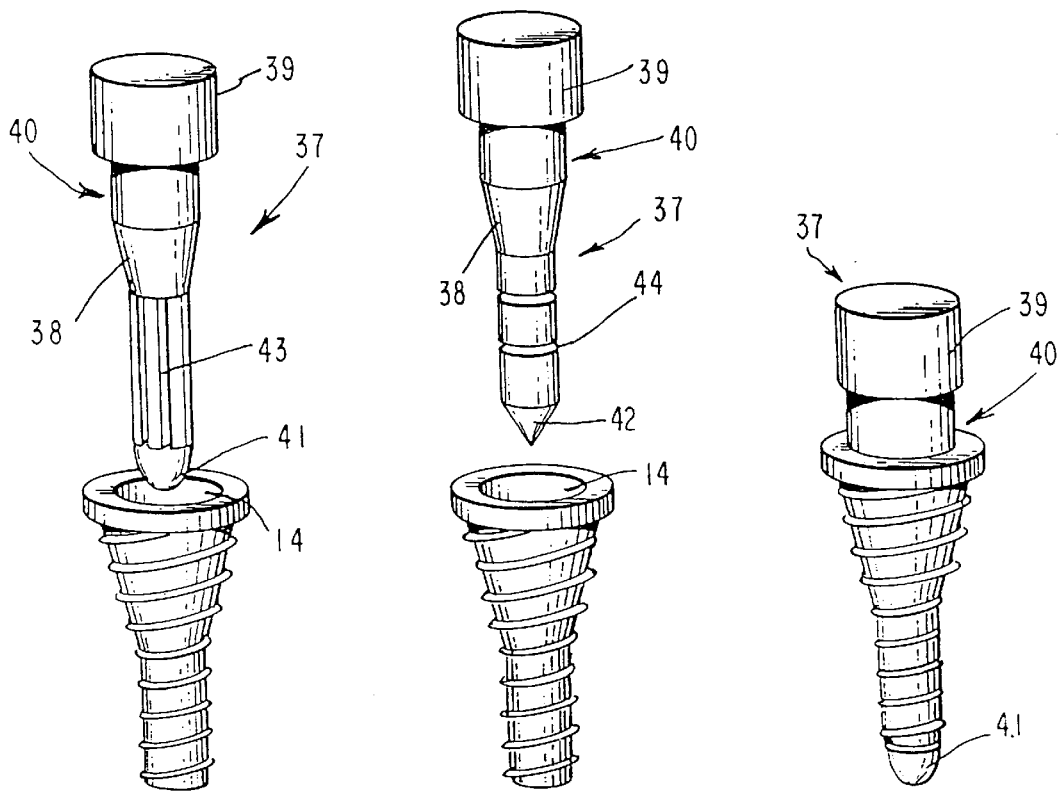
FIG. 9  FIG. 10  FIG. 11

SCREW-TYPE SKIN SEAL WITH INFLATABLE MEMBRANE

This application is a continuation-in-part of U.S. application Ser. No. 08/444,396, filed May 19, 1995, now U.S. Pat. No. 5,634,911 the disclosure of which is incorporated herein by reference.

FIELD OF THE INVENTION

This invention relates to the field of surgical endoscopy, specifically to improvements in skin seals and cannulas.

BACKGROUND OF THE INVENTION

Surgical endoscopy is a surgical technique of using small-diameter long-handled tools such as graspers, forceps, scissors, retractors, dissectors and clamps specially designed to be inserted through small incisions in the skin (or other openings in the body) to perform operations within the body. The surgeon performing the surgery often cannot see the operation directly, and must watch the procedure on a video monitor fed by an endoscopic camera or endoscope. Endoscopic surgery replaces open surgery, which requires large incisions, essentially opening the body cavity completely, in order to perform surgery deep within the body. Endoscopic techniques have been used for gall stone removal, gall bladder removal, hernia repair, tumor removal, lymph node removal and appendectomy and many other operations. Endoscopic surgery is also called laparoscopic surgery, video assisted surgery, minimally invasive surgery, and band-aid surgery, but throughout this specification the term endoscopic surgery or laparoscopic surgery will be used.

To illustrate the background of the inventions described below, the example of the laparoscopic cholecystectomy, hernia repair or lymphadenectomy, as well as the operation for harvesting a blood vessel, will be used to illustrate both the old laparoscopic procedures and the new laparoscopic procedures now possible with the new devices. In the old procedure, a working space was created in the abdomen using the process called pneumoperitoneum or insufflation. Insufflation is the process of injecting gas into the body to blow it up like a balloon, creating a chamber filled with gas. When performed on the abdomen, the peritoneum is inflated and the procedure is known as pneumoperitoneum. The procedure can be used for inflating a space between the peritoneum and the skin to permit laparoscopic hernia repair, as illustrated in U.S. Pat. No. 5,496,345 issued to Keiturakis et al. and entitled "An Expansible Tunneling Apparatus for Creating An Anatomic Working Space." Insufflation can be used also to inflate a tunnel shaped working space over a blood vessel, to facilitate blood vessel harvesting, as described in U.S. patent application Ser. No. 08/267,484 entitled "Extraluminal Balloon Dissection Apparatus and Method", incorporated herein by reference. While the chamber is filled with gas, the surgeon inserts long slender laparoscopic tools through trocars and cannulas which pierce the skin and provide access ports into the insufflated chamber.

For abdominal surgery such as a cholecystectomy (gall bladder removal), the insufflation is accomplished by the following procedure. An incision is made at the lower edge of the belly button or umbilicus. The surgeon uses his fingers or a blunt dissection tool such as a blunt nosed obturator to uncover the fascia or abdominal muscles, then a large needle, referred to as a Verres needle is inserted into the abdomen or peritoneal cavity. The Verres needle punctures the fascia and peritoneum which cover the abdomen. A pressurized gas such as $CO_2$ is injected into the abdomen through the needle, in effect inflating the abdomen like a balloon. After the abdomen is inflated, the Verres needle is removed. After the needle is removed, trocars and cannulas are inserted into the space created by the insufflation. Endoscopic instruments including an endoscope or laparoscope, scissors, graspers, etc., are inserted into the abdomen through the cannulas and manipulated to dissect tissue surrounding the gall bladder, remove the gall bladder, and stitch the internal wounds.

To harvest the saphenous vein using laparoscopic procedures, the surgeon may insufflate a tunnel shaped work space over a blood vessel. The tunnel is first created using obturators or tunneling devices or balloons inserted through small incisions along or over the saphenous vein. After the tunnel is created, the surgeon may insert skin seals and cannulas, and insufflation gas is injected through one of the trocars. While the tunnel is insufflated, the cannulas permit the surgeon to insert laparoscopic instruments into the tunnel to perform surgery on the saphenous vein.

The cannula used in the procedures described above is a length of rigid tube. The trocars and cannula are designed to allow laparoscopic instruments to pass through them and prevent gas from escaping the abdomen or other insufflated work space. The cannula may have a flapper valve or a trumpet valve inside which opens to allow an endoscope or laparoscope or other instrument to pass through, and valve closes when the laparoscope is removed. Some trocar/cannula devices also contain a duckbill valve to assist in sealing the trocar. The cannulas are typically about 6 inches or 15 centimeters long, and come in diameters matching various laparoscopic devices, generally from 2 to 15 mm.

Some surgeons use bare cannulas, secured only by a tight fit with the skin and fascia. However, cannulas frequently slip out of the body during use, disrupting the procedure and possibly endangering the patient. To prevent this danger, surgeons have devised a variety of methods to secure the cannula to the body and prevent it from slipping out of the body. Some cannulas are provided with threaded sleeves, fixed to the cannula. Some cannulas are provided with a threaded gripper with a smooth inner bore that matches the size of the cannula, so that the cannula can slide inside the gripper as shown in FIG. 2. The gripper stabilizes the cannula so that it will not slip out of the body inadvertently, but can be easily slipped out when the surgeon wants. The threaded gripper is simply screwed into the incision in the skin. This option permits the ready insertion and removal of smooth walled cannulas by sliding them in and out of the gripper. Other grippers have been used, such as the gripper with expandable arms, the gripper with inflatable balloon on the outside, and the Hasson cannula. These devices are illustrated in Oshinsky, et al., Laparoscopic Entry and Exit, reprinted in Urologic Laparoscopy at 91–101 (Das & Crawford ed. 1994). These devices are variously referred to as threaded skin seals, screw skin seals, skin anchors, obturators, grippers, trocar stabilizers or cannula stabilizers.

The surgeon usually needs to place several trocars and cannulas into the abdomen, and inserts as many as needed to accomplish the intended operation. The first cannula placed through the belly button is used to insert a laparoscope so that the placement of other trocars and cannulas can be viewed from inside the abdomen. After several cannulas are in place, the surgeon can view the procedure through any port, and can insert laparoscopic scissors, cutters and graspers and other tools through the cannulas in order to perform the surgery. The typical endoscopic graspers 3 used for stitching inside the abdomen are shown, deployed inside the cannulas, in FIG. 2. A bare cannula 4 is used with endoscopic graspers 3a. Another pair of laparoscopic graspers 3b is inserted into a cannula 4a which is inserted through a threaded gripper 5. A third cannula 6, shown with a threaded outer surface, is provided for an endoscope 34 which is inserted into the work space to provide the surgeon with a video view of the graspers and body tissue.

The arrangement of the cannulas and trocars is required because the abdomen must be inflated to make room for the surgeon to work. The small diameter of the cannulas keeps the incisions small, and the matching diameter of the laparoscopic instruments is necessary to prevent leakage of the insufflation gas from the abdomen. Laparoscopic instruments of various designs are available, and they generally are about 5 to 12 mm in diameter (to match the inside bore of the cannulas) and about 10 to 40 cm in length. They are long and therefore difficult to use, and they are usually used when the surgeon can see them only through the laparoscope. Modern laparoscopic procedures require the surgeon to view the procedure on a video monitor. It may take a surgeon a lot of practice before becoming comfortable and skillful with the laparoscopic graspers, grippers and scissors. These tools are more difficult to use than the surgical tools which every surgeon uses in normal surgery, such as those shown in FIG. 3, in use during open laparotomy. The normal graspers are shown in use while the surgeon is tying off a suture. This normal procedure is familiar to a large number of surgeons. The normal surgical graspers 7a and 7b are shown in use in FIG. 3, suturing body tissue 8 with suture 9, and it can readily be appreciated that the laparoscopic graspers shown in FIG. 2 require significantly more skill than the normal surgical tools. One of the drawbacks of the known cannulas and grippers is that they are adapted to admit only relatively narrow instruments, and are therefore generally unsuited for use with ordinary open-incision surgical tools.

It would be advantageous to use normal surgical tools during laparoscopic procedures, but this is usually not permitted by the typical construction of the trocars and cannulas which are too narrow, long and rigid to permit passage of the normal surgical tools. Most surgeons are very well trained in using conventional non-endoscopic instruments, such as the open-incision graspers shown in FIG. 3, and numerous procedures involving the graspers such as tying off a suture are well known and well practiced. The endoscopic instruments shown in FIG. 2, on the other hand, are not well known and well practiced, and generally require significantly more skill than the more familiar open-incision instruments. Thus, there is a need to provide cannulas and grippers which would accommodate the instruments used in open-incision procedures.

SUMMARY OF THE INVENTION

In a typical endoscopic or laparoscopic operation, a surgeon creates a working space inside the body through insufflation. To create the working space for abdominal surgery, the surgeon makes a small incision at, for example, the inferior margin of the umbilicus 1 as shown in FIG. 1, and then uses his fingers or a dissecting tool such as a blunt nosed obturator to prepare a point of injection. The surgeon then inserts a Verres needle 2 into the abdominal cavity, and causes a pressurized gas such as $CO_2$ to flow through the needle and into the abdominal cavity. This inflates the abdomen as shown in FIG. 1 and provides a working space for the surgeon. The needle may then be removed, and a cannula or trocar/cannula combination may be inserted into the incision. Additional incisions may also be made, and the first incision may be used to insert a laparoscope to assist in the placement of the other incisions. The additional incisions may each receive a cannula, and once several cannulas are in place the surgeon can view the procedure, and/or insert laparoscopic scissors, cutters, graspers or other tools through any of the cannulas.

As mentioned above, the trocars and cannulas can be used in endoscopic blood vessel surgery, laparoscopic cholecystectomy and laparoscopic hernia repairs where a work space is created under the skin. In the blood vessel harvesting operation where the saphenous vein is to be removed, a surgeon creates a tunnel between two small incisions over the saphenous vein. Then a cannula and skin seal are inserted into each incision. The tunnel is insufflated through one of the cannulas. In these procedures, the laparoscopic instruments are also inserted, into the working space through the cannulas, and the surgeon can watch the surgery through a laparoscope inserted through the one of the cannulas.

The devices presented herein allow for use of normal surgical tools (such as the forceps and scissors used in open-incision surgery) in laparoscopic procedures. The skin seal is fitted with one or more balloons on the inner bore. These balloons can be inflated after the skin seal is inserted into the incision into the abdomen. Placement of the skin seal can be accomplished as usual, with the aid of a blunt or sharp trocar or cannula placed within the threaded skin seal. Where the skin seal is flexible, the blunt or sharp trocar may include an circumferential lip about its distal end to prevent rollback of and streamline the distal end of the skin seal during placement of the skin seal. The threaded skin seal can be made of rigid plastic, as is customary, or preferably it may be made of soft and pliable material such as latex or silicone rubber. When the threaded skin seal is in place, the trocar may be removed and the balloon may be inflated until it expands to fill the inner bore of the threaded skin seal, thus sealing the bore to maintain the pressure created inside the abdomen with the insufflation gas. The balloons are soft and pliable and can conform around the elements of the instruments as they are moved about during use. Thus, normal or conventional surgical instruments may be passed between the balloons. Both normal surgical instruments and laparoscopic instruments may be inserted into the body through the balloons without disrupting the seal created by the balloons. The efficiency of the seal created by the balloon is further enhanced by the use of a plurality of tab-like or brush-like protrusions extending inwardly from the balloon to form a tortuous path type seal or labyrinth type seal. Alternatively, the protrusions may be inflatable.

The balloon is soft and pliable so that normal surgical tools may be operated inside the inflated balloon segments and the balloon segments will not hamper the operation of the tool to a significant degree. The skin seal may be provided with a balloon membrane that expands outside the lumen of the skin seal to create a dumbbell, dog bone or bowtie shaped balloon which pinches the skin and, when necessary, fills the lumen of the skin seal.

More than one tool may be inserted through a single skin seal because the balloons are sufficiently pliable and may be inflated to a lesser degree. In this manner, normal surgical instruments may be used in laparoscopic procedures, taking advantage of the fact that they are easier to use and more surgeons know how to use them, compared to the long laparoscopic instruments. The balloon filled skin seal may be used also as a seal for laparoscopic incisions which are no longer necessary or which the surgeon desires to plug temporarily while still leaving a skin seal in place for later use.

BRIEF DESCRIPTION OF THE DRAWINGS

FIGS. 6, 6a and 6b show cross sectional views of the cannula with the inflatable balloon shown in its inflated state.

FIGS. 7 through 7c show end views, from the proximal end, of the cannula with inflatable balloon inside.

FIG. 8 shows a pair of skin seals with the balloons inside, with normal surgical instrument inserted through the balloons, deployed in the manner of intended use.

FIG. 9 shows a blunt obturator suited for use with the skin seal.

FIG. 10 shows a sharp trocar type obturator suited for use with the skin seal.

FIG. 11 shows the blunt obturator inserted in the skin seal.

DETAILED DESCRIPTION OF THE DRAWINGS

The cannulas and grippers described below allow for use of normal surgical instruments in laparoscopic surgical procedures. The typical gripper configuration is modified by adding a balloon or inflatable membrane to the inner bore of the gripper and adding an inflation port to the wall of the gripper to allow for inflation of the balloon. When the balloon is inflated, it closes off the inner bore of the gripper, so that it provides an airtight seal during insufflation. The balloon is pliable so that tools can be inserted through the inner bore of the balloon and the balloon expands around the surgical tool to maintain the seal with little or no leakage of insufflation gas.

Figure 4:
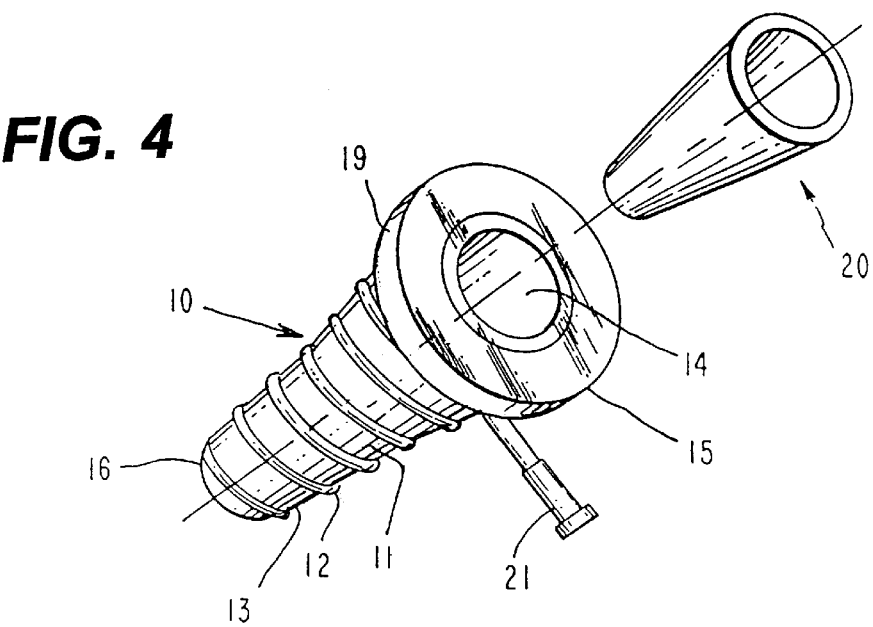
FIG. 4 is an exploded view of the cannula with an inflatable balloon inside.

Referring to FIG. 4, the threaded skin seal 10 is made of a funnel or tube 11 with a generally conical or frustum outer shape with screw threads 12 provided on the outer surface 13. The inner bore 14 is conical or funnel shaped, conforming generally to the outer shape of the skin seal overall, the skin seal 10 is funnel shaped, and the proximal end 15 of the threaded skin seal 10 has a large opening, and the distal or bottom end 16 has a smaller opening. The distal or bottom portion of the skin seal may have a straight or cylindrical outer shape to make it easier to screw the skin seal into an incision, and this straight section may be made of variable length to match the different thickness of fat which will be encountered in different patients. The proximal end preferably has a conical inner bore to facilitate insertion of tools into the opening and through the cannula, but the inner bore may be straight. The proximal end may also be described as flared, and may be gradually flared in relation to the distal end, as though trumpet shaped, or may be flared in a discrete fashion as in a typical funnel, with a straight tube at the distal end and a conical segment at the proximal end. The screw threads 12 constitute a fastening means, and may be replaced with other fastening means such as a circumferentially ribbed outer contour or a longitudinally grooved outer contour. As shown, a flange 19 may be provided on the proximal end 15 of the cannula for ease in handling. The flange 19 also provides a convenient means for mounting the bellows onto the cannula. The skin seal 10 is preferably 1 to 3 inches, or about 2 to 8 centimeters, long.

A balloon membrane 20 has a generally conical or frustum shape matching the inner bore 14 of the threaded skin seal 10 and having the same overall length of the threaded skin seal. The balloon membrane fits inside the threaded skin seal and is sealed to the skin seal funnel at the upper edge and lower edge of the balloon membrane. The balloon membrane may be shorter than the skin seal, and may be sealed to the inner surface of the skin seal at points inside the skin seal, rather than at the immediate distal and proximal edges of the skin seal. Also, the balloon membrane may be longer than the skin seal and may be cuffed or folded back around the outside of the skin seal at the proximal and distal ends, and sealed at the cuffs.

An inflation port 21 is provided (see also FIGS. 5 and 6), comprising a hole in the wall 22 of the threaded skin seal 10. An inflation tube 23 or Luer fitting connects the inflation port to a suitable pump such as the syringe 24 shown in FIG. 5 or the squeeze pump 25 shown in FIG. 6. Where the syringe 24 is used, the membrane 20 may be inflated and deflated repeatedly by pushing and pulling on the syringe plunger 26, thus forcing air into the bladder and sucking air out of the bladder. A one-way valve or stopcock may be used to seal the membrane so that the pump or syringe may be detached from the skin seal when not needed. Alternately, an inflation port can be provided at the distal tip of the skin seal, comprising an open airway between the inflatable membrane and the insufflated work space. In this manner, the insufflation gas enters the skin seal from inside the body to pressurize and inflate the inflatable membrane. In this manner, an automatic seal is created upon insertion of the skin seal into the insufflated space. This simplifies placement and use of the skin seal because there is no need for a separate syringe or pump to inflate the membrane.

In the preferred embodiment, the balloon membrane 20 is made of biocompatible elastomeric or elastic material such as latex, silicone rubber or any other suitable compliant material, elastic material or inflatable material. The cannula 10 is made of rigid or flexible material, soft or hard plastic, high density or low density polyethylene, polypropylene, thick latex, silicone rubber or any other suitable material including plastic, elastic or non-elastic biocompatible material.

Figure 5:
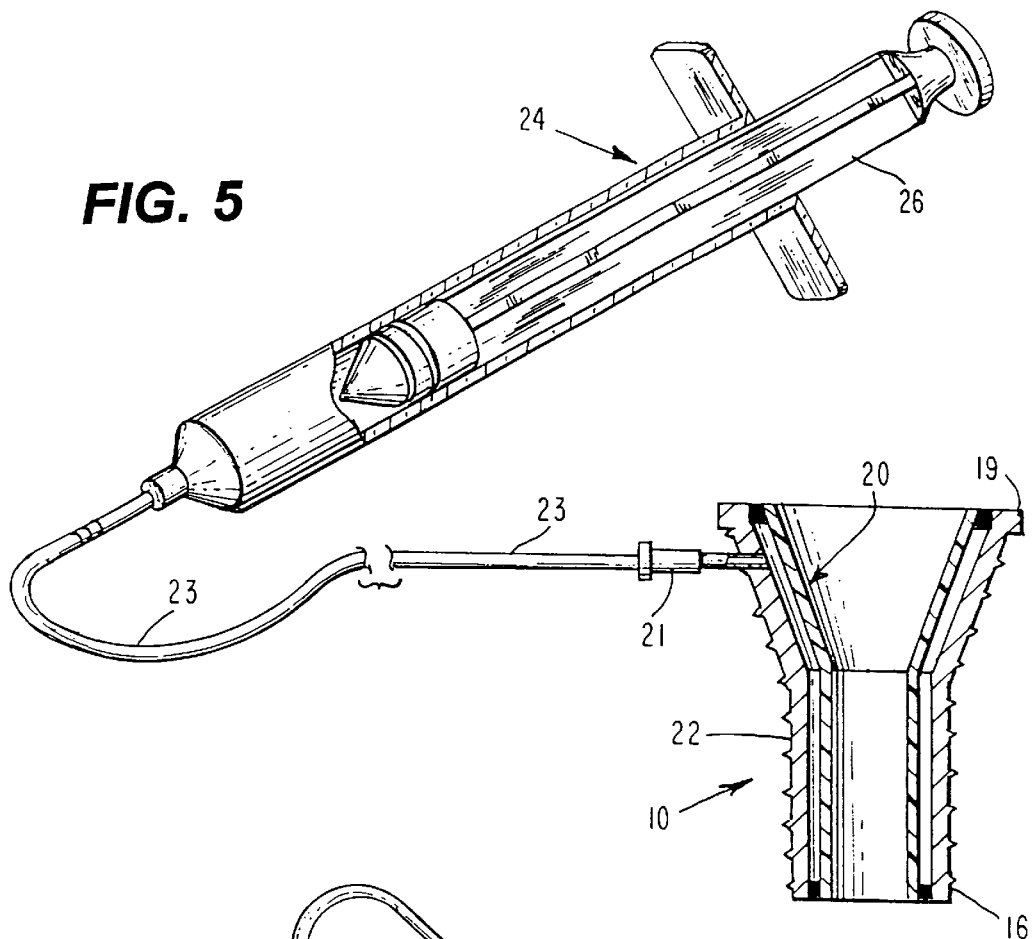
FIG. 5 is a cross sectional view of the cannula with the inflatable balloon inside.

As shown in FIGS. 4 and 5, the inflatable skin seal may be constructed by applying an elastic cylindrical or conical balloon membrane 20 to the inner bore of skin seal cannula 10 and sealing the distal end of the balloon 20 to the distal end 16 of the cannula 10 and sealing the proximal end of the balloon 20 to the proximal end 15 of the cannula 10, thereby creating an inflatable space between the cannula 10 and the membrane 20. Alternatively, a fully formed balloon bladder, comprising inner and outer conical membranes sealed to each other at their distal and proximal ends can be provided and fixed to the inner bore of the cannula. The overall shape of the balloon will be conical, funnel shaped or flared to match the shape of the inside of the skin seal. While one balloon is depicted in each of the figures, two or more balloons may be used to guard against the possibility of rupture and loss of insufflation pressure during an operation, or to facilitate manufacture, or to facilitate use of the skin seal with particular tools. A membrane seal may be provided at any cross sectional plane, within the skin seal, to guard against loss of insufflation pressure.

Figure 6:
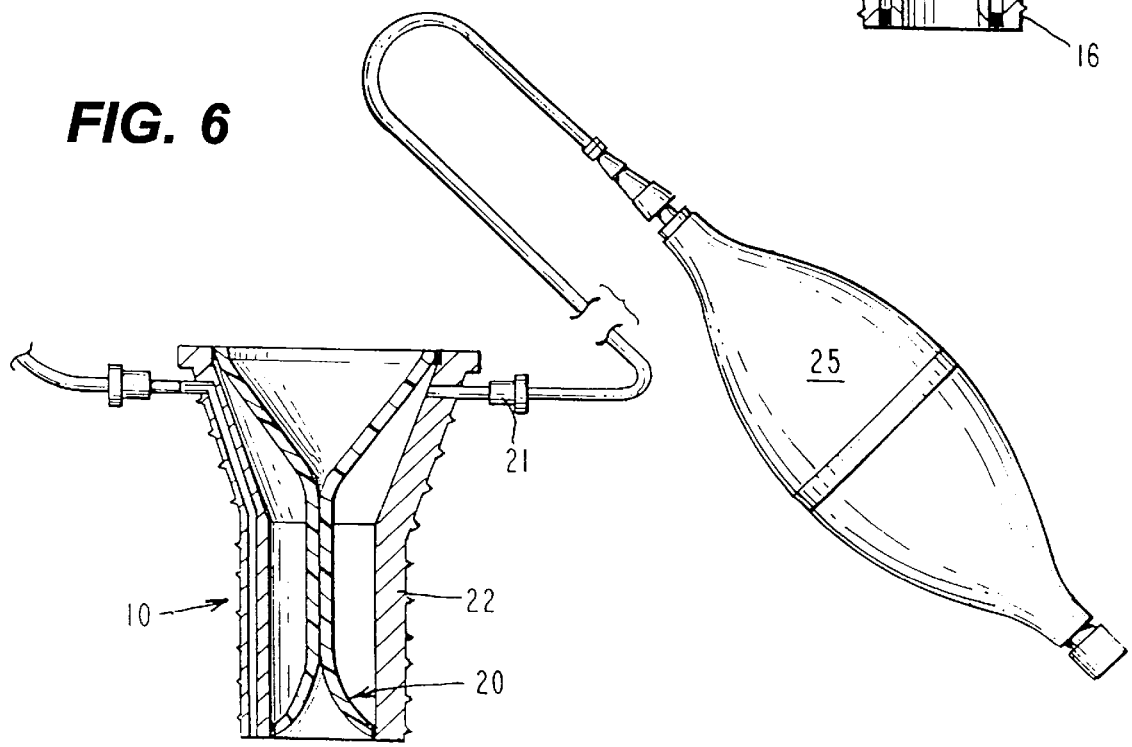

FIG. 6 shows the inflatable skin seal with the membrane in its inflated condition. The squeeze pump 25 is used to force air into the space between the balloon membrane 20 and the wall of the cannula, causing the membrane to inflate within the cannula. The inflated membrane can be inflated until it completely obstructs the inner bore of the cannula and provides an air-tight seal between the distal and proximal ends of the cannula. The cannula can be thinwalled and flexible enough to expand, as well, thereby further improving the seal between the cannula and the skin incision. As shown in FIG. 6a, the membrane need not extend for the full length of the cannula, but may instead be sealed to the inner bore at various points inside the cannula. The cannula in FIG. 6a has a balloon 20 only in the conical inner bore of the proximal section of the cannula, and this facilitates use of graspers, scissors and other such instruments which might pinch the balloon when operated, or unnecessarily reduce the internal diameter of the narrowest portion of the cannula. As shown in FIG. 6b, the wall of the cannula may be made flexible enough to expand outward when the skin seal is inflated, so that any gaps or looseness in the seal between the outside of the skin seal and the skin incision are closed by the expansion of the outer wall 22 of the skin seal.

FIG. 7 shows the view of the inflated membrane viewed from the proximal end of the cannula. The membrane naturally bulges in two or more radial sections or segments 27 to fill the lumen of the cannula. The expansion of the balloon sections need not be controlled, but may be controlled to facilitate operation of graspers or other hinged and pinching tools. For example, the application of restrictors, comprised of thickened strips 50 and 51 along the length of the membrane, shown in FIG. 7a, may be applied to the membrane to inhibit expansion along the strip. Wire bands, plastic bands, or a line of adhesive gluing the balloon membrane to the skin seal may also be used to prevent expansion of the membrane along a longitudinal line of the membrane extending from the proximal end (or near the proximal end) to the distal end (or near the distal end) of the funnel. In this manner, a uniform expansion can be obtained, with the membrane expanding from the walls of the cannula to meet along a uniform plane. A pinching tool used in the cannula can be opened and closed along the plane defined by the inflated balloons, and the balloon will pliantly close upon the lumen but allow the pinching tool to open and close with less chance of pinching and cutting the balloon. As shown in FIG. 7b, the inflatable membrane 20 may be placed on the inner bore of the skin seal in an eccentric manner, covering only a portion of the inner wall of the skin seal. FIG. 7c shows the eccentric inflatable membrane in its inflated state.

FIG. 8 shows the skin seals 28, 29 and 30 with the balloon membranes inflated. Skin seal 28 has the funnel shape described above. A pair of normal surgical scissors such as Metzenbaum scissors 31 is inserted through one skin seal 28 and a pair of normal surgical graspers 7 (examples include Kelly clamps, Kelly placenta forceps, and Mayo clamps) is inserted through the skin seal cannula 29 to perform operations beyond the distal tip of the cannula. The skin seals are shown screwed into incisions through skin 32 and subcutaneous fat 33, and they may also extend through the peritoneum or other tissue when appropriate to the operation. An endoscope or laparoscope 34 which can be inserted through one skin seal to provide a view of the procedure is shown in the central skin seal 30. Because the balloon is pliable and conforms around any device within the skin seal, the graspers may be manipulated inside the cannula without breaking the insufflation seal. As the graspers are manipulated, the membrane conforms around graspers but yields to allow the graspers to be open, closed, twisted, pushed and pulled within the skin seal without substantially degrading the seal created by the membrane. It should be noted that a perfectly airtight seal is not necessary, and some leakage of insufflation gas or fluid is acceptable, so long as insufflation gas or fluid can be injected at a rate sufficient to make up for any losses. Where the cannula itself is made of a soft pliant material such as latex rubber or silicone rubber, the forceps may be manipulated even further, and deformation of the skin seal 28 will permit a wider range of motion for the forceps. Skin seal 28 is shown with a pair of conventional surgical scissors 31 or shears disposed through the skin seal. The scissors may be opened wide, as shown, and the distal or proximal end of the skin seal will yield and flare out to allow operation of the scissors through their full range of motion and opened through the full throw (the "throw" referring to the length of arc 35 over which the graspers or scissors may be opened) of scissors 31 or graspers, as illustrated by flared distal portion 36 of skin seal 28.

Figure 1:
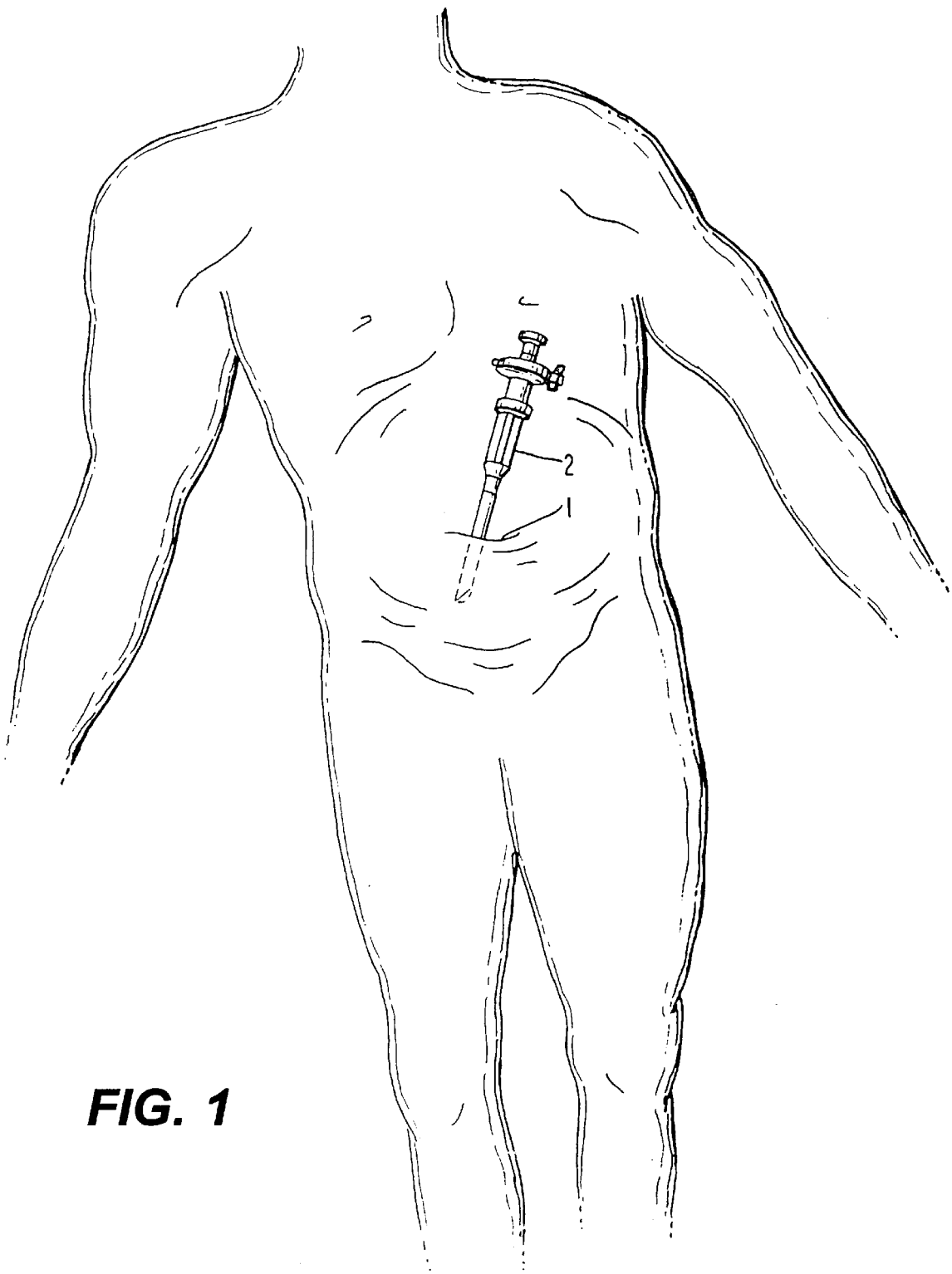
FIG. 1 is an external view of the abdomen of a patient undergoing insufflation.
Figure 2:
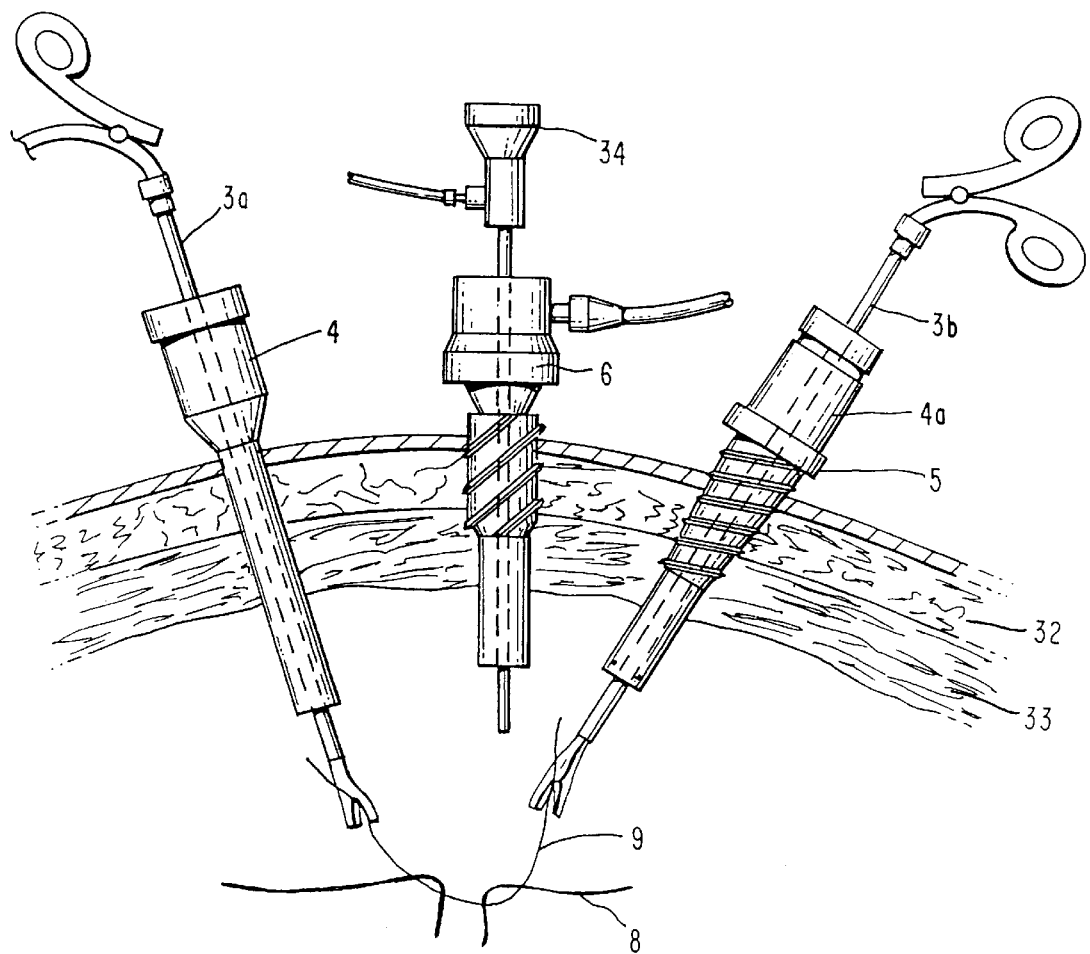
FIG. 2 is a cross section drawing of the insufflated abdomen of a patient with several trocars, cannulas and laparoscopic instruments in place for a laparoscopic procedure.
Figure 3:
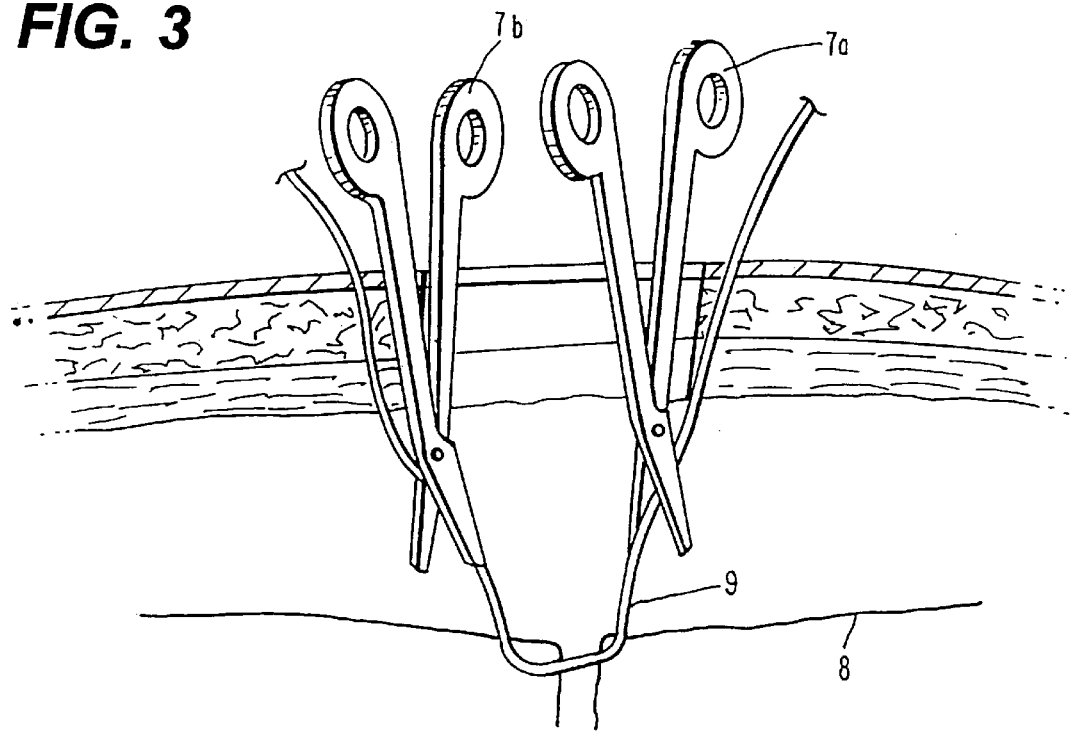
FIG. 3 is a view of an open laparotomy procedure using normal surgical forceps.

It will be readily appreciated that such operation would not be possible using standard cannulas. The normal surgical tools are much easier to use than the long laparoscopic instruments shown in FIG. 2. Also, the tools can be much larger, and have much larger operating implements. For example, the cutting edges of scissors 31 are much longer than cutting edges on laparoscopic scissors, and can cut much more quickly. A common method of dissecting tissue with normal scissors is to pierce connective tissue with the closed scissors and open the scissors, operating the scissors in backwards fashion, so that the dull outer edges of the scissors pull connective tissue apart. This can be done very quickly using the skin seals 28, 29 and 30, as compared to slow and tedious snipping required when using long laparoscopic instruments.

Placement of the skin seals may be facilitated with special blunt obturators shown in FIGS. 9, 10 and 11. The blunt obturator 37 provides support for the skin seal as it is pushed and screwed into the incision. The blunt obturator comprises a peg 38 with an outer contour which matches the inner bore of the skin seal, a handle 39, a finger gap 40, and a blunt tip 41. The tip may be blunt and rounded, or it may be sharp and pointed, as illustrated by the sharp pointed trocar type tip 42 in FIG. 10, in which case the sharp point 42 can puncture body tissue. The obturator is placed inside the skin seal as shown in FIG. 11, and the assembly is screwed into the body as a unit. After the skin seal is in place, the obturator is removed to allow insertion of other devices into the skin seal. The finger gap 40 leaves some space for the surgeon to push against the flange of the skin seal while pulling the handle 39, thus avoiding the possibility that the skin seal will be pulled out of the body with the obturator. Because the obturator fits tightly inside the skin seal to give it support during insertion, it may inadvertently become sealed to the inside of the skin seal, especially if there is any leakage of body fluids or water into the skin seal. Any excessive force required to pull out the obturator could result in pulling the screw skin seal out of the skin incision. To prevent the need for such excessive force, the portion of the obturator which fits inside the skin seal may be provided with vacuum breakers in the form of scored lines or channels 43, circumferential grooves 44, or a roughened surface, to prevent a vacuum from forming between the skin seal inflatable membrane. The scoring or roughening may take any form.

Figures 12, 13, 14, 15:
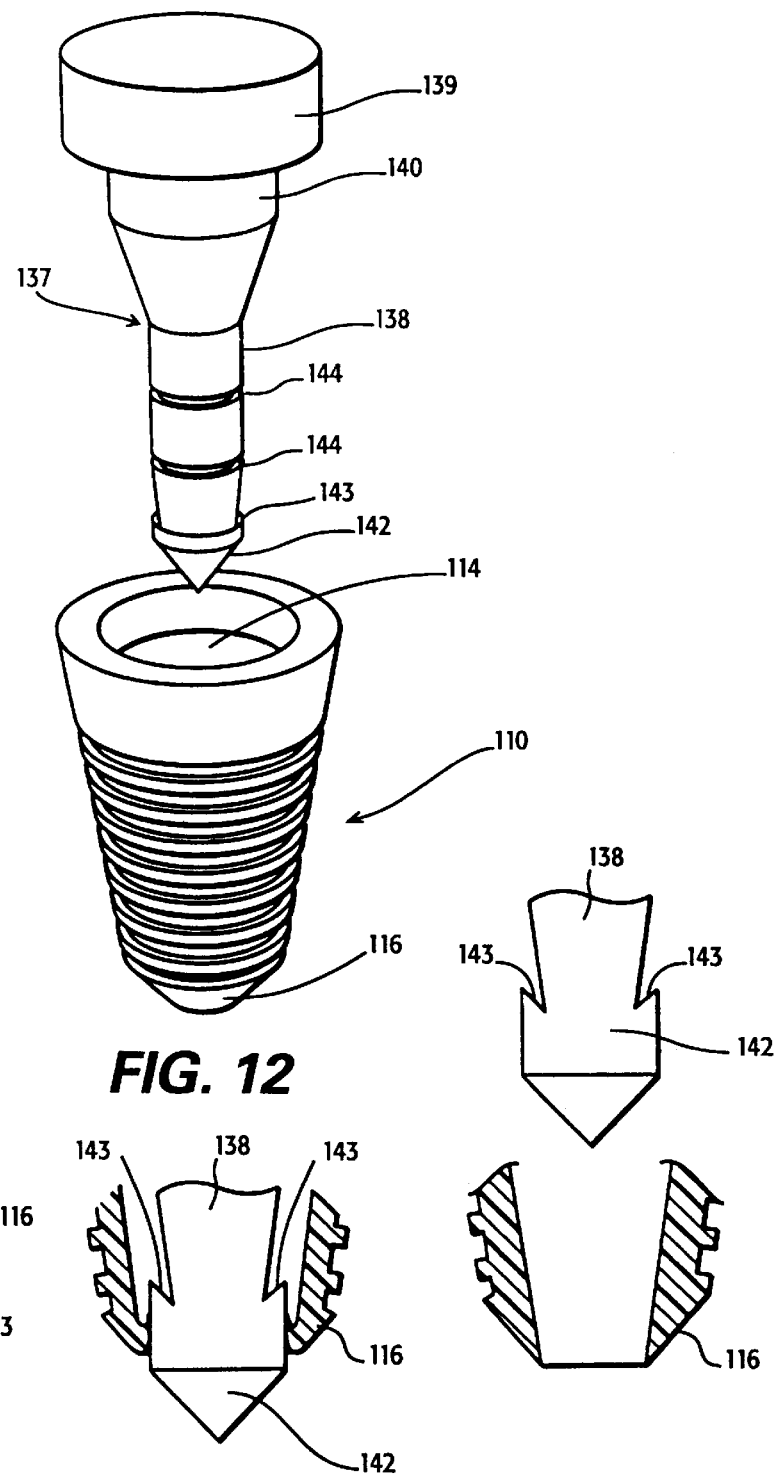
FIG. 12 shows an exploded view of a sharp trocar type obturator with a skin seal.
FIG. 13 shows a partial cross-sectional view of the sharp trocar obturator inserted in the skin seal.
FIG. 14 shows a partial cross-sectional view of the sharp trocar obturator being withdrawn from the skin seal.
FIG. 15 shows a partial cross-sectional and exploded view of the sharp trocar obturator withdrawn from the skin seal.

Placement of flexible skin seals may be facilitated with an alternative obturator or trocar shown in FIGS. 12–15. The obturator 137 provides support for the skin seal 110 while protecting the distal end 116 of the skin seal 110 from rollback or inversion as it is pushed through the body tissue and screwed into place. The obturator 137 comprises a peg 138 with an outer contour that matches portions of the inner bore 114 of the skin seal 110, a handle 139, a finger gap 140, vacuum venting circumferential grooves 144, and a sharp-pointed trocar tip 142. The upper portion of the tip 142 includes an upwardly angled member 143 forming a circumferential lip about the peg 138. The obturator 137 is placed inside the skin seal 110 as shown in FIG. 14 with the tip of the distal end 116 of the skin seal being received in the recess formed between the circumferential lip 143 and the peg 138. As the assembly is screwed into the body as a unit, the circumferential lip 143 prevents the tip of the distal end 116 of the skin seal 110 from rolling up or curling back on the obturator 137 and increasing the insertion resistance and damaging the skin seal. After the skin seal is in place, the obturator is removed. As the obturator is drawn upwardly through the skin seal, the tip of the distal end 116 of the skin seal curls inwardly as the pointed tip 142 of the obturator is pulled past the distal end 116 of the skin seal. Once the obturator is removed, the distal end 116 of the skin seal 110 springs back to its normal position to allow insertion of other devices into the skin seal.

Figure 16:
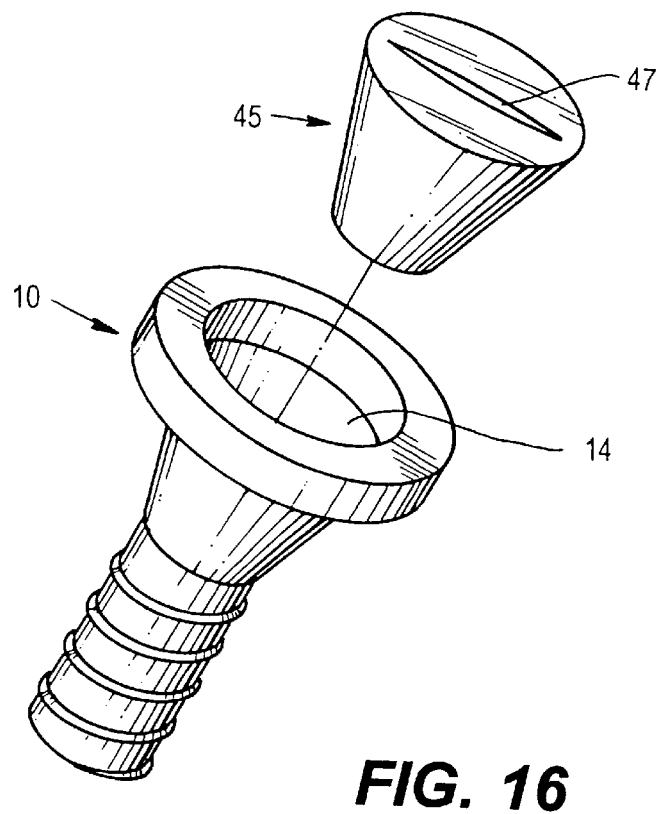
FIGS. 16 and 16a show the skin seal with compressible packing.
Figure 16A:
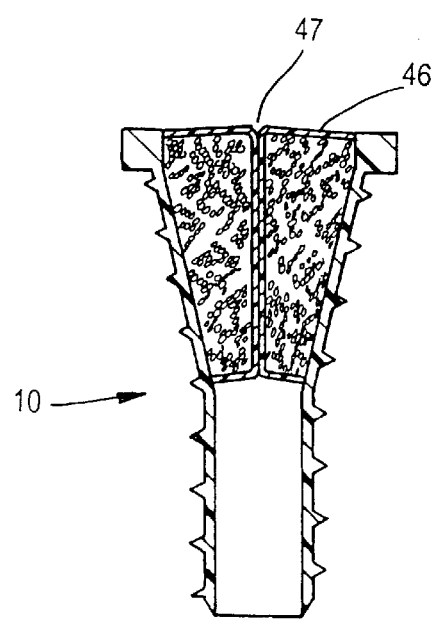

An alternative embodiment of the screw-type skin seal uses a resilient packing in the lumen of the skin seal cannula. As shown in FIGS. 16 and 16a, the lumen 14 of the skin seal 10 is filled with resilient or compressible packing 45 made of a closed cell foam. The foam may have a thin skin 46 characteristic of closed cell foams. Alternately, the packing may be made of any resilient foam material and the skin 46 may be replaced with a layer of plastic or elastic material. The packing may also be made of a gel, gel-filled membrane, or extremely soft rubber or other very low durometer material capable of elastically conforming around the surgical instruments. The packing is formed to fit into the skin seal, and is preferably slightly oversized so that it is compressed when inserted and sealed to the inside of the skin seal cannula. The packing is provided with a narrow slit, or a closed slit 47 through which surgical instruments may be inserted into the body. When surgical instruments are pushed through the slit in the packing, the packing resiliently conforms around the instrument to obtain an airtight seal around the instrument. When inserted through a skin incision into an insufflated work space in the body, the skin seal with resilient packing accomplishes a substantially airtight seal of the incision, thus maintaining insufflation while allowing use of normal open surgery instruments in the endoscopic procedure. As with the inflatable membrane embodiments, this embodiment may be used with the normal open surgery graspers and scissors, as well as endoscopic and laparoscopic instruments, during endoscopic surgery.

Figure 17:
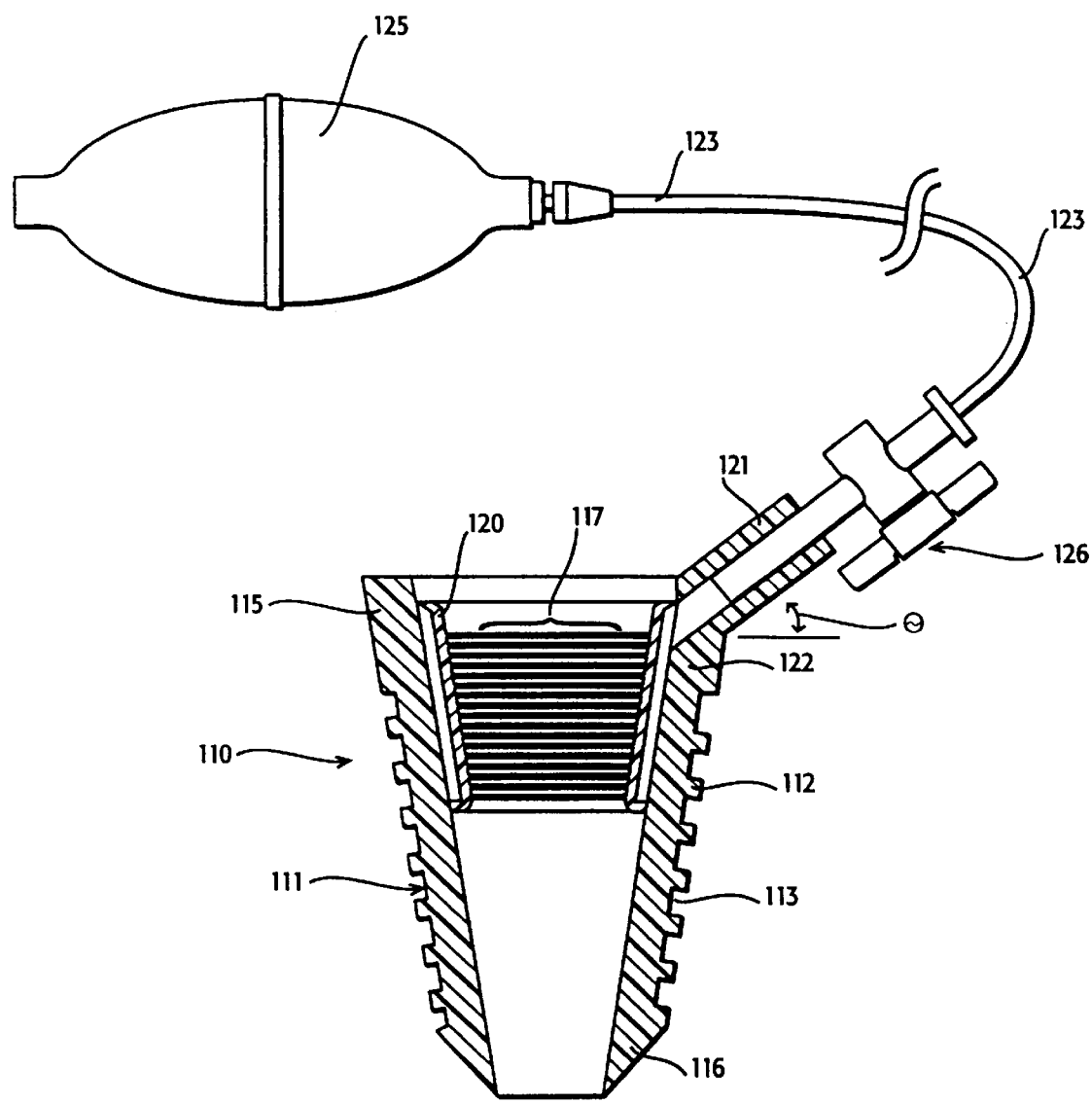
FIG. 17 is a cross-sectional view of the skin seal with an inflatable balloon membrane and a plurality of protrusions. The skin seal is interconnected to a squeeze pump.

Referring to FIG. 17, an alternative threaded skin seal 110 is made of a flexible tube 111 with a generally continuously tapered outer shape with screw threads 112 provided on its outer surface 113. The inner bore 114 also has a continuously tapered shape, conforming generally to the outer shape of the skin seal. Overall, the skin seal 110 is shaped such that the proximal end 115 of the threaded skin seal 110 has a larger opening than the opening of the distal or bottom end 116.

A balloon membrane 120 has a generally continuously tapered shape matching a portion of the inner bore 114 of the threaded skin seal 110. The balloon membrane 120 fits inside the threaded skin seal 110 and is sealed to the inner surface of the skin seal 110 at the upper and lower edges of the balloon membrane 120. The balloon membrane 120 may be shorter than the skin seal 110, and thus may be sealed to the inner surface of the skin seal 110 at various points inside the skin seal 110. Also, the balloon membrane 120 may be longer than the skin seal 110 and may be cuffed or folded back around the outside of the skin seal 110 at the proximal and distal ends 115 and 116, and sealed at the cuffs.

An inflation port 121 extends from the wall 122 of the threaded skin seal 110 and communicates with the balloon membrane 120 through a hole in the wall 122. Preferably, the inflation port 121 extends upwardly from the wall 122 of the skin seal at an angle θ to a horizontal plane formed by a cross-section of the skin seal 110. Preferably, the angle θ is in the range of about 30° to 70°. This configuration advantageously provides access to the inflation port 121 when the skin seal is screwed into the body tissue of a patient regardless of the patient's body type and/or angle of entry. In an obese patient, a radially extending inflation port may be obstructed by the patient's excess fatty body tissue. However, if the inflation port 121 is angled as shown in FIG. 17, access to the inflation port 121 will tend to be unobstructed even in obese patients.

An inflation tube 123 or Luer fitting connects the inflation port 121 to a squeeze pump 125. In addition, a one-way valve or stopcock 126 may be used to seal the balloon membrane 120 so that the squeeze pump 125 may be detached from the skin seal 110 when not needed.

Figure 18:
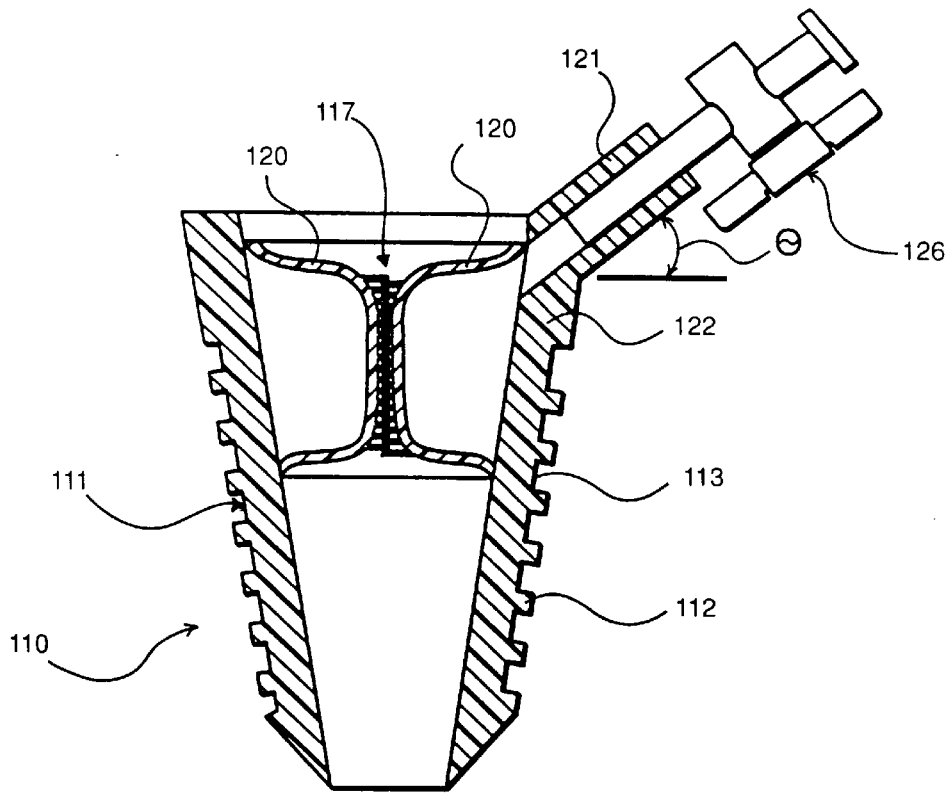
FIG. 18 is a cross-sectional view of the skin seal in FIG. 17 with the inflatable balloon membrane shown in its inflated state with the protrusions forming a labyrinth type seal.
Figure 19:
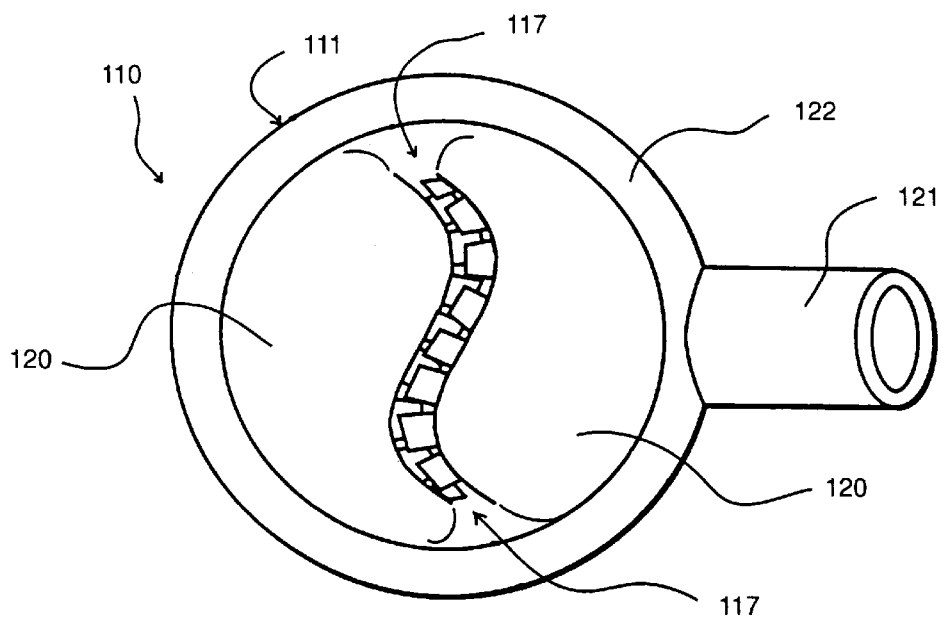
FIG. 19 is a top view of the skin seal in FIG. 18.
Figure 20:
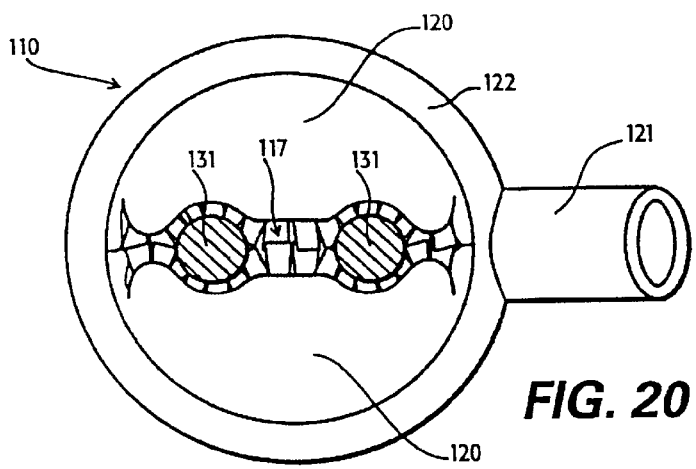
FIG. 20 shows a top view of the skin seal in FIG. 18 having a surgical scissors inserted therein.

To provide a more efficient seal, a plurality of tabbed protrusions 117 extend inwardly from the balloon membrane 120 in a helical pattern along the balloon membrane or in a series of rings longitudinally spaced along the balloon membrane 120. The squeeze pump 125 is used to force air into the space between the balloon membrane 120 and the wall 122 of the skin seal 110, causing the balloon membrane 120 to inflate within the skin seal 110 (see FIGS. 18 and 19). As the balloon membrane 120 is inflated to obstruct the inner bore 114 of the skin seal 110, the tabbed protrusions 117 tend to overlap one another forming a tortuous path or labyrinth type seal between the inflated segments of the balloon membrane 120. The tabbed protrusions 117 also tend to form a tortuous path type seal about the arms of a surgical scissors 131 when positioned within the skin seal 110 (see FIG. 20).

Figure 21:
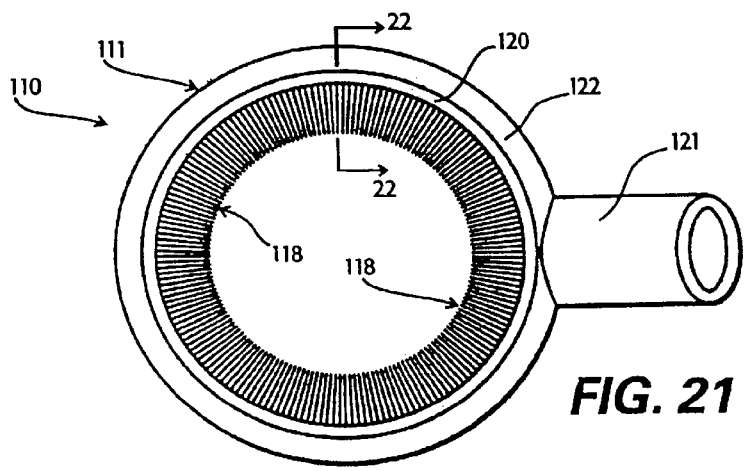
FIG. 21 shows a top view of the skin seal in FIG. 17 having an alternate type of protrusions extending inwardly from the inflatable balloon membrane.
Figure 22:
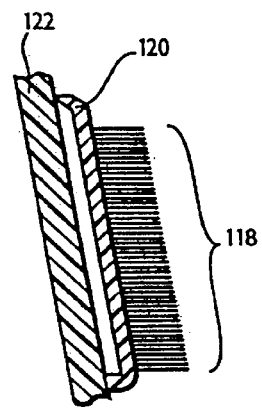
FIG. 22 is a cross-sectional view taken along line 22—22 in FIG. 21.

As shown in FIGS. 21–24, alternative methods may be used to create a tortuous path type seal between the inflated segments of the balloon membrane 120. Turning to FIGS. 21 and 22, a plurality of bristle-like brush members 118 extend inwardly from the balloon membrane 120 to form a tortuous path type seal when the balloon membrane 120 is inflated. To enhance the effectiveness of the seal when using the bristle-type brush members 18, a surgical gel or fluid can be applied to the brush members 118.

Figure 23:
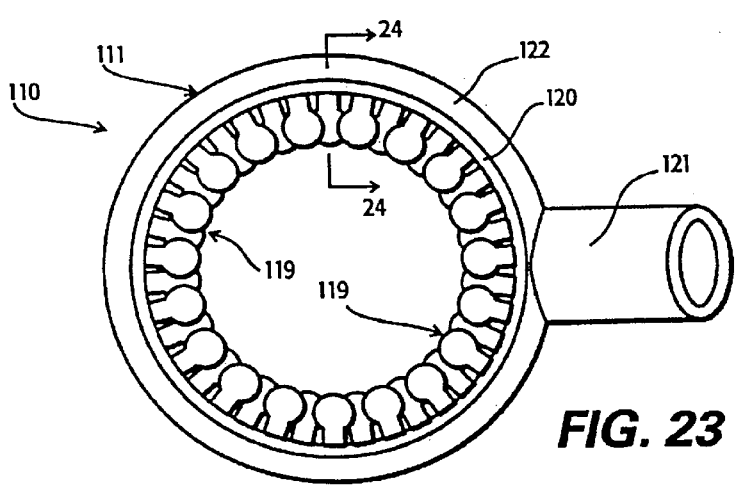
FIG. 23 is a top view of the skin seal in FIG. 17 having an alternate type of protrusions extending inwardly from the inflatable balloon membrane.
Figure 24:
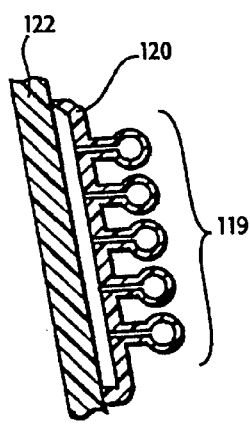
FIG. 24 is a cross-sectional view taken along line 24—24 in FIG. 23.

Turning to FIGS. 23 and 24, a plurality of balloon-type protrusions 119 may be used to extend inwardly from the balloon membrane 120. The balloon protrusions 119 may be positioned in a helical pattern along the balloon membrane 120 or in a series of rings longitudinally spaced along the balloon membrane 120. The balloon protrusions 119 are in communication with the interior of the balloon membrane 120 such that when the balloon membrane 120 is inflated, the balloon protrusions are likewise inflated so as to form a tortuous path type seal between inflated segments of the balloon membrane 120.

The skin seals described above can be used for any endoscopic or laparoscopic surgery to permit use of normal surgical instruments, i.e., ordinary open-incision surgical instruments. While the skin seals described above are useful in procedures requiring insufflation, they may also be used in other endoscopic or laparoscopic procedures. The use of the skin seal in any endoscopic or laparoscopic procedures will allow deployment of normal surgical tools while protecting the area of the incision from trauma caused by the operation of the surgical instruments. Where insufflation or flushing is required, the bladder in the skin seal may be inflated to prevent undesired flow out of the cannula. Also, although the skin seal described above has been described in the best known embodiments, fabricated with suitable materials to the inventors, the particular materials and shapes depicted in the illustrations may be altered and improved upon without departing from the inventions as claimed. It is specifically contemplated that the materials be improved upon. Furthermore, although the devices have been described in relationship to surgery requiring insufflation and endoscopic or laparoscopic surgery, the claimed devices and methods may be used in surgical and non-surgical applications wherever the features of these device and methods prove beneficial.

What is claimed is:

1. A skin seal comprising:
   a tube having a proximal end, a distal end, an outer surface, and an inner bore, said proximal end having a larger outer diameter than said distal end forming a continuous taper therebetween;
   an inflatable membrane disposed within said inner bore of said flexible tube; and
   an inflation port extending from a wall of said flexible tube and in communication with said inflatable membrane.

2. The skin seal of claim 1 further comprising a plurality of protrusions extending inwardly from said inflatable membrane.

3. The skin seal of claim 2 wherein said plurality of protrusions comprise a plurality of tabs.

4. The skin seal of claim 2 wherein said plurality of protrusions comprise bristle-like brush members.

5. The skin seal of claim 2 wherein said plurality of protrusions are inflatable.

6. The skin seal of claim 1 further comprising screw threads on said outer surface of said flexible tube.

7. The skin seal of claim 1 wherein the tube is flexible.

8. The skin seal of claim 1 wherein the tube is substantially rigid.

9. A skin seal comprising
   a flexible tube having a proximal end, and distal end, an outer surface and an inner bore, said proximal end having a larger outer diameter than said distal end forming a continuous taper therebetween,
   an inflatable membrane disposed within said inner bore of said flexible tube, said inflatable membrane having a plurality of protrusions extending inwardly therefrom, and
   an inflation port extending from a wall of said flexible tube and communicating with said inflatable membrane, said inflation port extending upwardly at an angle.

10. The skin seal of claim 9 wherein said plurality of protrusions comprise a plurality of tabs.

11. The skin seal of claim 9 wherein said plurality of protrusions comprise bristle-like brush members.

12. The skin seal of claim 9 wherein said plurality of protrusions are inflatable.

13. A skin seal comprising:
   a flexible tube having a proximal end, a distal end, an outer surface, and an inner bore;
   an inflatable membrane disposed within said inner bore of said tube; and
   a plurality of protrusions extending inwardly from said inflatable membrane, said plurality of protrusions engaging one another to form a seal upon inflation.

14. The skin of seal of claim 13 further comprising an inflation port extending from a wall of said flexible tube and communicating with said inflatable membrane through an inflation passageway in said wall of said flexible tube.

15. The skin seal of claim 14 wherein said inflation port is angled upwardly from said wall.

16. The skin seal of claim 13 wherein said plurality of protrusions comprise a plurality of tabs.

17. The skin seal of claim 13 wherein said plurality of protrusions comprise a plurality of bristle-like brush members.

18. The skin seal of claim 13 wherein said plurality of protrusions are inflatable.

19. The skin seal of claim 13 wherein said proximal end has a larger outer diameter than said distal end forming a continuous taper therebetween.

20. The skin seal of claim 13 further comprising screw threads formed on said outer surface of said flexible tube.

21. A skin seal comprising:
   a tube having a proximal end, a distal end, an outer surface, and an inner bore;
   an inflatable membrane disposed within said inner bore of said tube;
   a plurality of protrusions extending inwardly from said inflatable membrane, said plurality of protrusions adapted to engage a medical instrument inserted through said inner bore and to form a seal around said medical instrument upon inflation of said inflatable membrane; and plurality of protrusions on said outer surface adapted to engage the tissue surrounding an incision being sealed.

22. The skin seal of claim 21 further comprising an inflation port extending from a wall of said tube and communicating with said inflatable membrane through an inflation passageway in said wall of said flexible tube.

23. The skin seal of claim 22 wherein said inflation port is angled upwardly from said wall.

24. The skin seal of claim 21 wherein said plurality of protrusions extending inwardly comprise a plurality of tabs.

25. The skin seal of claim 21 wherein said plurality of protrusions extending inwardly comprise a plurality of bristle-like brush members.

26. The skin seal of claim 21 wherein said plurality of protrusions extending inwardly from said inflatable member are inflatable.

27. The skin seal of claim 21 wherein said proximal end has a larger diameter than said distal end forming a continuous taper therebetween.

28. The skin seal of claim 21 wherein said plurality of protrusions on said outer surface comprises screw threads.

29. The skin seal of claim 21 wherein the tube is flexible.

30. The skin seal of claim 21 wherein the tube is substantially rigid.

31. A skin seal comprising:
   a flexible tube having a proximal end, a distal end, an outer surface, and an inner bore, said inner bore extending between the proximal end and the distal end;
   an inflatable membrane disposed within said inner bore of said flexible tube;
   a plurality of protrusions on said outer surface adapted to engage the tissue surrounding an incision being sealed; and
   an inflation port extending from a wall of said flexible tube and in communication with said inflatable membrane.

32. The skin seal of claim 31 further comprising a plurality of protrusions extending inwardly from said inflatable membrane.

33. The skin seal of claim 32 wherein said plurality of protrusions extending inwardly comprise a plurality of tabs.

34. The skin seal of claim 32 wherein said plurality of protrusions extending inwardly comprise bristle-like brush members.

35. The skin seal of claim 32 wherein said plurality of protrusions extending inwardly are inflatable.

36. The skin seal of claim 31 wherein said proximal end has a larger outer diameter than said distal end forming a continuous taper therebetween.

37. The skin seal of claim 31 wherein said plurality of protrusions on said outer surface comprises screw threads.

38. A skin seal comprising:
   a tube defining a central axis having a proximal end, a distal end, an outer surface and an inner bore;
   an inflatable membrane disposed within said inner bore of said tube;
   an inflation port extending from a wall of said tube and in communication with said inflatable membrane, said inflation port extending proximally at an acute angle to said tube at an intersection with said tube; and a plurality of protrusions on said outer surface adapted to engage the tissue surrounding an incision being sealed.

39. The skin seal of claim 38 further comprising a plurality of protrusions extending inwardly from said inflatable membrane.

40. The skin seal of claim 39 wherein said plurality of protrusions comprise a plurality of tabs.

41. The skin seal of claim 39 wherein said plurality of protrusions comprise bristle-like brush members.

42. The skin seal of claim 39 wherein said plurality of protrusions are inflatable.

43. The skin seal of claim 38 wherein said proximal end has a larger outer diameter than said distal end forming a continuous taper therebetween.

44. The skin seal of claim 38 wherein said plurality of protrusions on said outer surface comprises screw threads.

\* \* \* \* \*